United States Patent
Litovitz

(10) Patent No.: US 8,014,846 B2
(45) Date of Patent: *Sep. 6, 2011

(54) METHODS OF USING MAGNETIC FIELDS TO UNIFORMLY INDUCE ELECTRIC FIELDS FOR THERAPEUTIC PURPOSES

(75) Inventor: Theodore A. Litovitz, Annapolis, MD (US)

(73) Assignee: The Catholic University of America, Washington, DC (US)

( * ) Notice: Subject to any disclaimer, the term of this patent is extended or adjusted under 35 U.S.C. 154(b) by 94 days.

This patent is subject to a terminal disclaimer.

(21) Appl. No.: 12/534,172

(22) Filed: Aug. 3, 2009

(65) Prior Publication Data

US 2009/0292159 A1    Nov. 26, 2009

Related U.S. Application Data

(60) Division of application No. 11/055,984, filed on Feb. 14, 2005, now Pat. No. 7,587,230, which is a continuation-in-part of application No. 10/426,720, filed on May 1, 2003, now Pat. No. 6,856,839, which is a division of application No. 09/737,546, filed on Dec. 18, 2000, now Pat. No. 6,853,864.

(60) Provisional application No. 60/179,738, filed on Feb. 2, 2000.

(51) Int. Cl.
    *A61B 5/05* (2006.01)
(52) U.S. Cl. .................................... 600/409
(58) Field of Classification Search ............ 600/409, 600/407, 408

See application file for complete search history.

(56) References Cited

U.S. PATENT DOCUMENTS

| | | | |
|---|---|---|---|
| 4,800,899 A | 1/1989 | Elliott |
| 4,815,446 A | 3/1989 | McIntosh |
| 5,312,534 A | 5/1994 | Liboff et al. |
| 5,450,859 A | 9/1995 | Litovitz |
| 5,544,665 A | 8/1996 | Litovitz |
| 5,566,685 A | 10/1996 | Litovitz |
| 5,780,971 A | 7/1998 | Dawson et al. |
| 5,968,527 A | 10/1999 | Litovitz |

(Continued)

FOREIGN PATENT DOCUMENTS

EP    0 966 988 A1    12/1999

OTHER PUBLICATIONS

Aquino DA, et al., "Multiple sclerosis: altered expression of 70- and 27-jDa heat shock proteins in lesions and myelin," J. Neuropathol. Exp. Neurol. 1997:56(6):664-672.

(Continued)

*Primary Examiner* — Daniel L Robinson
(74) *Attorney, Agent, or Firm* — Vedder Price P.C.; Ajay A. Jagtiani

(57) ABSTRACT

The present invention provides a method and apparatus for delivering an electric field to a body by delivering a first magnetic field from a first coil in a first orientation to a body and directed at a desired target within the body, and delivering a second magnetic field from a second coil in a second orientation directed at the desired target within the body to induce an electric field across the desired target, wherein only one magnetic field is delivered to the body at any one time.

17 Claims, 4 Drawing Sheets

U.S. PATENT DOCUMENTS

| | | | |
|---|---|---|---|
| 6,142,939 | A | 11/2000 | Eppstein et al. |
| 6,238,872 | B1 | 5/2001 | Mosseri |
| 6,246,912 | B1 | 6/2001 | Sluijter et al. |
| 6,251,128 | B1 | 6/2001 | Knopp et al. |
| 6,259,952 | B1 | 7/2001 | Sluijter et al. |
| 6,301,506 | B1 | 10/2001 | den Boer et al. |
| 6,331,774 | B1 | 12/2001 | Stern |
| 6,348,070 | B1 | 2/2002 | Teissel et al. |
| 6,451,013 | B1 | 9/2002 | Bays et al. |
| 6,539,245 | B2 | 3/2003 | Tsukada et al. |
| 6,561,968 | B1 | 5/2003 | Dissing et al. |
| 6,595,934 | B1 | 7/2003 | Hissong et al. |
| 6,853,864 | B2 | 2/2005 | Litovitz |
| 6,856,839 | B2 | 2/2005 | Litovitz |
| 7,587,230 | B2 * | 9/2009 | Litovitz ..................... 600/409 |

OTHER PUBLICATIONS

Birnbaum G, et al., "Heat shock or stress proteins and their role as auto-antigens in multiple sclerosis," Ann. NY Acad. Sci. 1997;835:157-167.

Blank M, et al., "Changes in polypeptide distribution stimulated by different levels of electro-magnetic and thermal stress," Bioelectrochemistry and Bioenergetics 1994;33:109-114.

Boehncke WH, et al., "Differential expression heat shock protein 70 (HSP7O) and heat shock cognate proteins 70 (HSC7O) in human epidermis," Arch. Dermatol. Res. 1994; 287(1):68-71.

Borrelli MJ, et al., "Thermotolerance expression in mitotic CHO cells without increased translation of heat shock proteins," J. Cell Physiol. 1988;169:420-8.

Cadossi R, et al., "Effect of low frequency low energy pilsing electromagnetic fields on mice injected with cyclophosphamide," Exp. Hematol. 1991;19:196-201.

Chang BK, et al., "Inhibition of DNA synthesis and enhancement of theuptake and action of methotrexate by low —power-density mucrowave radiation in L1210 leukemic cells," Cancer Res. 1980;40:1002-1005.

Currie RW, et al., "Heat-shock response is associated with enhanced postischemic ventricular recovery" Circ.Res. 1988;63:543-549.

Detlavs I, et al., "Experimental study of the effects of radiofrequency electromagnetic fields on animals with soft tissue wounds," Sci.Total. Environ. 1996;180:35-42.

Di Carlo AL, et al., Myocardial protection conferred by electromagnetic felds,) Circulation 1999;99:813-816.

Di Carlo AL, et al., "Short-Term Magnetic Field Exposures (60 Hz) Induce Protection Against Ultraviolet Radiation Damage," Int.J. Radiat.Biol. 1998;75: 1541-1550.

Dindar H, et al., "The effect of electromagnetic field stimulation in corticosteroidsinhibited intestinal wound healing," Tokai,J,Exp.Clin. Med. 1993; 18:49-55.

Donnelly TJ, et al., "Heat shock protein induction in rat hearts. A role for improved myocardial salvage after ischemia and reperfusion?, " Circulation 1992;85:769-778.

Essele KP, et al., "Coil optimization for neural stimulation with magnetic field," in Electricity and Magnetism in Biology and Medicine, Blank M, Ed. San Francisco Press, Inc. CA. p. 736-7, 1993.

Fitzsimmons RJ, et al., "Embryonic bone matrix formation is increased after exposure to a low- amplitude capacitively coupled electric field, in vitro," Biochim. Biophys. Acta 1986;882:51-56.

Fuks Z, et al., "Basic fobroblast growth factor protects endothelial cells against radiation-induced programmed cell death in vitro and in vivo," Cancer Res. 1994;54:2585-90.

Goodman R, et al., "Increased levels of HSP7O transcripts induced when cells are exposed to low frequency electromagnetic fields," Bioelectrochemistry and Bioenergetics 1994;33:115-120.

Gordon, SA, et al., "Induction of heat shock protein 70 protects thymocytes against rasiation-induced apoptosis,"Arch. Surg. 1997; 132: 1277-82.

Han L, et al., "Application of magnetic field-induced heat shock protein 70 for presurgical cytoprotection," J.Cell Biochem. 1998;71:577-583.

He L et al., "Variation of heat chock pretein 70 through the cell cycle in HL-60 cells and its relationship to apoptosis," Exp. Cell Res. 1997;232:64-71.

Hutter MM, et al., "Heat-shock protein induction in rat hearts. A direct correlation between the amount of heat-shock protein induced and the degree of myocardial protection," Circulation 1994:89:355-360.

Iwaki K, et al., "Induction if HSP7O in cultured rat neonatal cardiomyocytes by hypoxia and metabolic stress," Circulation 1993;87:2023-2032.

Kang KI, et al., "Luciferase activity and synthesis of Hsp9O are insensitive to 50Hz electromagnetic fields," Life Sci. 1998;63:489-97.

Korner G, et al., "Effects of ionizing irradiation on endothelial cell transqlutaminase," FEBS Lett. 1993;330:41-5.

Lin H, et al., "Electromagnetic field exposure induces rapid, transitory heat shock factoractivation in human cells" J. Cell Biochem. 1997;66:482-488.

Martin DF, et al., "Radiation sensitivity of cultured rabbit aortic endothelial cells," IJROBP 1984;10:1903-6.

Matsumoto H, et al., "Suppression of heat-induced p53 accumulation and activation byCDDP orx-rays in human glioblastoma cells," Int. J. Oncol. 1998;13(4):741-7.

McCleary VL, et al., "Low magnetic field effects on embryonic bone growth," Biomed.Sci.Instrum. 1991;27:205-217.

McMillan DR, et al., "Targeted disruption of heat transcription factor I abolishes thermotolerance and protection against heat-inducible apoptosis," J. Biol. Chem. 1998;273:7523-8.

Mestril R, et al., "Expression of inducible stress protein 70 in rat heat myogenic cells confers protection against simulated ischemia-induced injury," J.Clin.Invest. 1994;93:759-767.

Mestril R, et al., "Heat shock proteins and protection against myocardial ischemia," J.Mol.CellCardiol. 1995;27:45-52.

Miyakoshi, J.M., et al., "Long-term Exposure to a Magnetic Field (5 mT at 60Hz) Increases X-ray-induced Mutations," J. Radiat. Res., 1999;40: 13-21.

Morimoti R, et al., "Cell-specific expression of heat shock proteins in chicken reticulocytes and lymphocytes," J.Cell Biol. 1984;99: 1316-1323.

Omote Y, et al., "Treatment of experimental tumors with a combination of a pulsing magnetic field and an antitumor drug," Jpn. J. Cancer Res. 1990;81:956-961.

O'Rourke JF, et al., "X-irradiation- and carcinogen-induced proteins in cultured CHO cells," Biochem. Soc. Trans. 1992;20(1):745.

Pasquinelli P, et al., "Biological effects of PEMF (pulsing electromagnetic field): An attempt to modify cell resistance to anticancer agents," J. Environ. Pathol. Toxicol. Oncol. 1993;12(4):193-197.

Qi F, et al., "Functional and morphological damage of endothelium in rabbit ear artery following irradiation with cobalt 60," Br. J. Pharmacol. 1998;123:653-60. Ritossa FM, "A new puffing pattern induced by heat shock and DNP in Drosophila," Experentia 1962;18:571-573.

Ritossa FM, "A new puffing pattern induced by heat shock and DNP in Drosophila," Experentia 1962, 18:571-573.

Ruiter GA, et al., "Alkyl-lysophospholipids activate the SAPKIJNK pathway and enhance radiation-induced a o tosis," Cancer Res. 1999;59:2457-63.

Salvatore JR, et al., "Non-ionizing electromagnetic radiation: A study of carcinogenic and cancer treatment potential," Rev. Environ. Health 1994; 10(3-4):197-207.

Samali A, et al., "Heat shock proteins increase resistance to apoptosis," Exp. Cell Res. 1996;223(1):163-170.

Schett G, et al., "Enhanced expression of heat shock protein 70 (hsp7o) and heat shock factor 1(HSFI) activation in rheumatoid arthritis synovial tissue," J. Clin. Invest. 1998;102(2):302-311.

Strasser A, et al., "Bcl-2 and thermotolerance cooperate in cell survival," Cell Growth Differ. 1995;6:799-805.

Svedenstal, B.-M., et al., Lymphoma development among mice exposed to X-rays and pulsed magnetic fields, Int. J. Radiat. Biol., 1993, vol. 65, No. 1, 119-125.

Szigeti G, et al., "Effects of Bimoclomal, the novel heat shock protein con-induced, in dog ventricular myocardium," Life Sci. 2000;67:73-79.

Tosi P, et al., "Reduction of heat-shock protein-70 after prolonged treatment with retinoids: biological and clinical implications," Am.J. Hematol. 1997;56(3):143-150.

Trautinger F, et al., "Over expression of the small heat shock protein, hsp27, confers resistance to hyperthermia, but not to oxidative stress and UV-induced cell death, in a stably transfected squamous cell carcinoma cell line," J. Photochem. Photobiol. B.1997;39:90-5.

Tyrrell RM, "UV activation of mammalian stress proteins," EXS 1996;77:255-271.

Ueno S, et al., "Vectorial magnetic stimulation of the human brain," in Electricity and Magnetism in Biology and Medicine, Blank M. Ed. San Francisco Press, Inc. CA. p. 733-4, 1993.

Walker DM, et al., "Heat stress limits infarct size in the isolated perfused rabbit heart," Cardiovasc. Res. 1993;27:962-967.

Walleczek, J., et al, "Increase in Radiation-Induced HPRT Gene Mutation Frequency after Nonthermal Exposure to Nonionizing 60 Hz Electromagnetic Field," Radiation Research 151, 489-97 (1999).

Walter RJ, et al., "60-Hz electric fields inhibit protein kinase C activity and multidrug resistance gene (MDRI) up-regulation," Rad. Res. 1997; 147:369-75 Watters D, "Molecular mechanisms of ionizing radiation-induced apoptosis," Immunol. Cell Biol. 1999;77:263-71.

Watters D, "Molecular mechanisms of ionizing radiation-induced apoptosis," Immunol. Cell Biol. 1999;77:263-71.

Xu M, et al., "Intracellular distribution of hsp7o during long duration moderate hyperthermia," Int. J. Hyperthermia 1998;14:211-25.

* cited by examiner

METHODS OF USING MAGNETIC FIELDS TO UNIFORMLY INDUCE ELECTRIC FIELDS FOR THERAPEUTIC PURPOSES

CROSS-REFERENCE TO RELATED APPLICATIONS

This application is a divisional of application Ser. No. 11/055,984, filed Feb. 14, 2005, now U.S. Pat. No. 7,587,230, which is a continuation-in-part of application Ser. No. 10/426,720, filed May 1, 2003, now U.S. Pat. No. 6,856,839, which is a divisional of application Ser. No. 09/737,546, filed Dec. 18, 2000 now U.S. Pat. No. 6,853,864, which claims priority from U.S. Provisional Application No. 60/179,738, filed Feb. 2, 2000. The entire contents and disclosures of the above applications are incorporated herein by reference.

BACKGROUND

1. Field of the Invention

The present invention relates generally to the use of magnetic fields, and more particularly, to methods of using magnetic fields to uniformly induce electric fields for therapeutic purposes.

2. Related Art

Exposure to electromagnetic fields (EMFs) has become an increasingly useful tool in the treatment of many medical conditions. For example, exposure to time-varying magnetic fields is an accepted method of accelerating bone and wound healing. For example, EMFs may be used to limit damage to a heart during a heart attack and to protect bone marrow during chemotherapy and x-ray therapy for destruction of tumors.

When an EMF is applied to a cell, the electric field acting on the cell is the main mechanism by which the EMF affects the cell. For most purposes, the use of a low frequency time-varying magnetic field is the most convenient and controllable method of causing an electric field to appear across the tissue to be treated. A time-varying magnetic field may be created external to the body (for example with a pair of coils and a time-varying current source). When this field enters a body, it induces (by Faraday's Law) a time-varying electric field. It is fairly straightforward to create a uniform magnetic field in a body because the body's magnetic properties are quite uniform. However, the induced electric field is very non-uniform because the body's electrical conductivity may vary enormously from organ to organ (e.g., lung to heart) and within an organ (e.g., heart muscle to heart blood).

This lack of uniformity represents a serious limitation in the therapeutic application of time-varying magnetic fields. A good example of this limitation is in the use of magnetic fields to limit damage to the heart after an ischemic event (e.g., heart attack). Application of the magnetic field for a period of 30 minutes or more induces activation of heat shock proteins (hsps) in the cells of the heart muscle. These hsps act to protect the heart from cell death (necrosis) during the period in which the stoppage of blood flow (ischemia) causes cell stress. The problem that exists with this technique is that the induced electric fields vary so greatly that in many regions of the heart the induced electric field is not great enough to cause the cells to produce hsps. For example, the lung is a high resistance region adjacent to the heart. As a result, if the induced electric field passes through both the lung and heart, most of the field will appear across the lung and very little in the heart. Even if the induced electric field is applied in a direction that does not cross the lung, there will be regions in the heart that do not experience a significant electric field because the blood has such a low conductivity relative to the heart muscle.

Which regions of an organ do not experience a significant electric field depends critically upon the direction of the applied magnetic field, and thus the direction of the induced EMF. One proposed solution may be to simply apply fields in the x, y and z directions simultaneously. This however does not work since the vector sum of these fields would be simply a new magnetic field in a single direction.

SUMMARY

According to a first broad aspect of the present invention, there is provided a method of delivering an electric field to a body, comprising delivering a polarized magnetic field in a first direction to a body and directed at a desired target within the body; and changing the delivery direction of the magnetic field to a second direction directed at the desired target to induce an electric field across the desired target.

According to a second broad aspect of the present invention, there is provided a method of delivering an electric field to a body, comprising delivering a first magnetic field from a first coil in a first orientation to a body and directed at a desired target within the body; and delivering a second magnetic field from a second coil in a second orientation directed at the desired target within the body to induce an electric field across the desired target, wherein only one magnetic field is delivered to the body at any one time.

According to a third broad aspect of the present invention, there is provided a method of delivering an electric field to a body, comprising delivering a first magnetic field from a first coil in a first orientation to a body and directed at a desired target within the body; delivering a second magnetic field from a second coil in a second orientation directed at the desired target within the body; and delivering a third magnetic field from a third coil in a third orientation directed at the desired target within the body to induce an electric field across the desired target.

According to a fourth broad aspect of the present invention, there is provided an apparatus for delivering an electric field to a body, comprising a means for delivering a first magnetic field from a first coil in a first orientation to a body and directed at a desired target within the body; a means for delivering a second magnetic field from a second coil in a second orientation directed at the desired target within the body to induce an electric field across the desired target; and a means for alternating a current between the first coil and the second coil.

BRIEF DESCRIPTION OF THE DRAWINGS

The invention will be described in conjunction with the accompanying drawings, in which.

DETAILED DESCRIPTION

Figure 1:
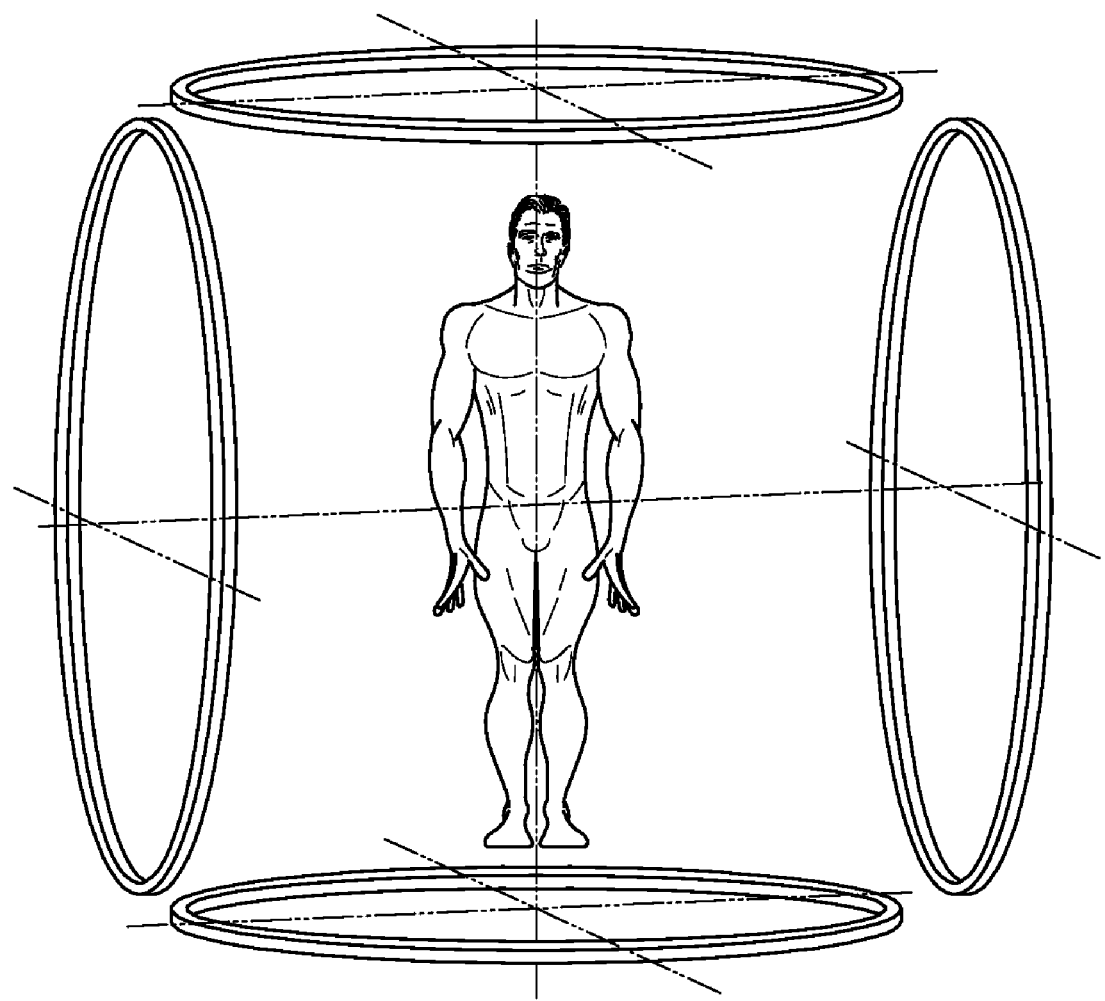
FIG. 1 is a schematic representation of a coil arrangement in accordance with an embodiment of the present invention in which 2 pairs of coils are oriented perpendicular to each other.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes of the present invention, the term "linearly polarized magnetic field" refers to a magnetic field that varies in time but whose direction is always directed along a given fixed line.

For the purposes of the present invention, the term "circularly polarized magnetic field" refers to a magnetic field whose field vector rotates about a fixed axis and appears to go around in a circle.

For the purposes of the present invention, the term "linear vertical field" refers to a linearly polarized field whose field vector is oriented in the vertical direction.

For the purposes of the present invention, the term "linear horizontal field" refers to a linearly polarized field whose field vector is oriented in the horizontal direction.

For the purposes of the present invention, the term "circular vertical field" refers to a circularly polarized field in which the field vector rotates about the vertical axis.

For the purposes of the present invention, the term "circular horizontal field" refers to a circularly polarized field in which the field vector rotates about the horizontal axis.

For the purposes of the present invention, the term "uniform electric field" refers to an induced electric field which is essentially constant in all of the tissues to be treated.

For the purposes of the present invention, the term "orientation" refers to the arrangement, configuration, direction, etc. of the element identified, such as the orientation of the magnetic field.

DESCRIPTION

The present invention provides a method and apparatus for delivering an electric field to a body by delivering a first magnetic field from a first coil in a first orientation to a body and directed at a desired target within the body, and delivering a second magnetic field from a second coil in a second orientation directed at the desired target within the body to induce an electric field across the desired target, wherein only one magnetic field is delivered to the body at any one time. The present invention provides an increase in the uniformity of the induced electric field. Increased uniformity is beneficial because, if the induced electric field is not uniform, its value may (in some regions of the tissue to be treated) fall below the threshold value necessary to induce beneficial biological effects, and thus the treatment may be only partially effective.

Under certain conditions, the effectiveness of a magnetic field treatment (whose duration may be, for example, from approximately 30 to approximately 60 minutes duration) may be significantly enhanced if the direction of the magnetic field direction is changed in time during the treatment.

A linearly polarized magnetic field may be used that alternately switches back and forth from one direction (e.g., vertical) to a perpendicular direction (e.g., horizontal). In other embodiments of the present invention, the direction of the field may be switched approximately 90 degrees +/−30 degrees with respect to the original direction of the field.

According to embodiments of the present invention, the timing of the exposure is an important element of an effective treatment. According to an embodiment of the present invention, the magnetic field remains in any given direction for at least 5 seconds before switching to a new direction. In some embodiments, the minimum time of exposure in any direction is greater than 10 seconds before switching. In some embodiments of the present invention, the maximum time of exposure in any direction is 300 seconds or more before switching. Thus, a suitable duration for exposure in any one direction may be from approximately 5 seconds to approximately 300 seconds or more, preferably from approximately 10 to approximately 30 seconds. The timeframes for exposure may be modified depending on the tissues or cells being treated, the frequency of exposure, and depending on the length of time between treatments.

Figure 2:
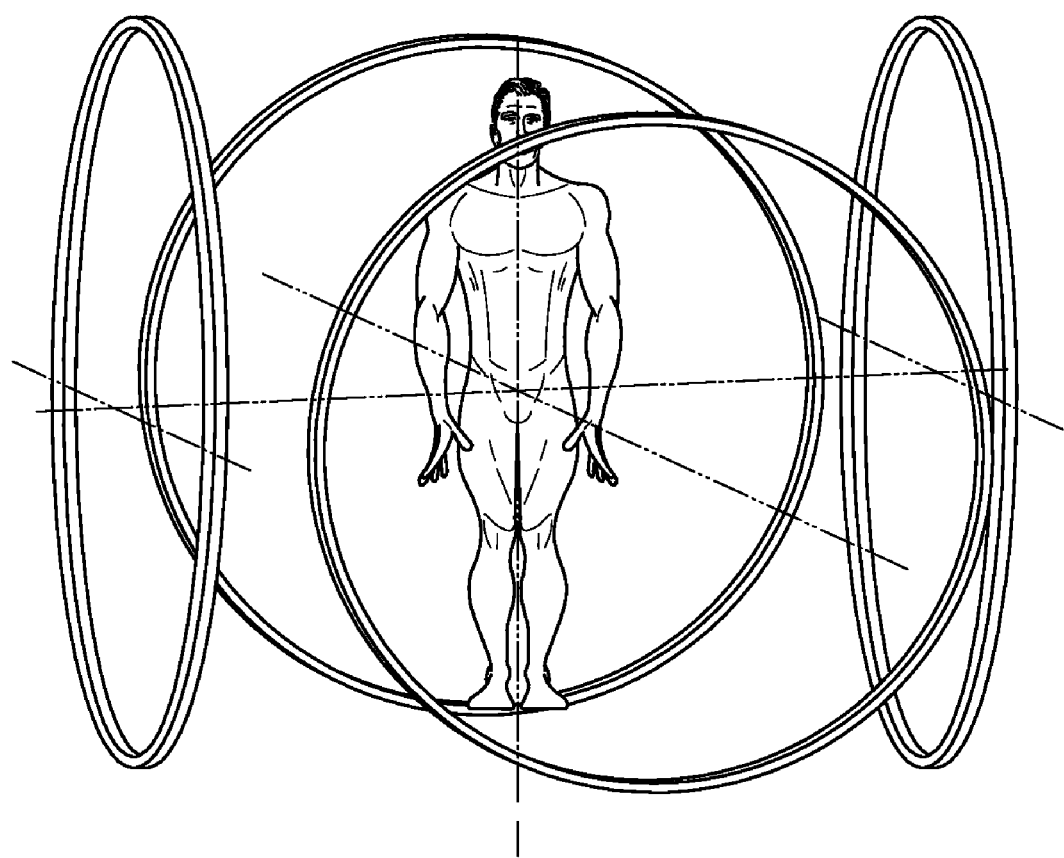
FIG. 2 is a schematic representation of a coil arrangement in accordance with an embodiment of the present invention in which 2 pairs of coils are oriented perpendicular to each other.

A magnetic field for use in the present invention may be generated with, for example, 2 pairs of coils that are oriented perpendicular to each other and in which an AC current alternately flows in one pair and then in the perpendicular pair. Such an arrangement provides a field in two perpendicular directions. FIGS. 1 and 2 provide schematic representations of coil arrangements in accordance with embodiments of the present invention in which 2 pairs of coils are oriented perpendicular to each other.

One goal of the present invention is to obtain a uniform induced electric field. Thus, according to an embodiment of the present invention, it is preferable to start with a reasonably uniform magnetic field. Current flowing in a single coil may be used in the present invention, although such an arrangement creates a relatively non-uniform magnetic field, thus introducing some of the problems mentioned above. A pair of coils which lie in planes that are perpendicular to each other yields much more uniform magnetic fields when current flows in them in such a way that the fields of the two coils are additive in the region between the coils.

In another arrangement of the present invention, two pairs of coils are arranged perpendicular to each other and the AC current in one pair is 90 degrees out of phase with the other pair of coils so that a circular polarized magnetic field is created. According to embodiments of the present invention, the currents may be other than 90 degrees out of phase, such as 90 degrees +/−30 degrees. If the currents are out of phase, but not 90 degrees out of phase, then the resultant field may be considered to be composed of a circular polarized field (caused by that component of the currents which are 90 degrees out of phase) and a linearly polarized magnetic field (caused by the component of the currents which are in phase with each other). This is generally less effective than the 90 degree out of phase condition, however, such an arrangement is encompassed within the scope of the present invention. Thus, for example, a magnetic field is created which rotates from, for example, the vertical direction to the horizontal direction continuously. Such an arrangement provides a field in two perpendicular directions.

Another embodiment of the present invention provides for a circular polarized magnetic field in which the circular field has a plane with a direction that is switched in time to a perpendicular direction. This may be accomplished with 3 pairs of coils oriented perpendicular to each other. Such an arrangement may be seen in FIG. 3. These coils may be designated coil pair 302, coil pair 304 and coil pair 306, respectively. In an exemplary embodiment of the present invention, AC current flows first in coil pairs 302 and 304. The currents in these coils may be 90 degrees out of phase. After a period of time, which is, for example, at least approximately 5 seconds, preferably greater than approximately 10 seconds, but typically not greater than approximately 300 seconds, the current is switched so that coil pair 302 and coil pair 306 are energized with or without 90 degree out of phase currents. In an embodiment of the present invention, coil pair 304 and coil pair 306 are also 90 degrees out of phase. Such an arrangement provides a field in three perpendicular directions.

According to embodiments of the present invention, the frequency of the applied magnetic field is at least approximately 20 Hz. In other embodiments of the present invention, the frequency of the applied magnetic field may be approximately 20 Hz to approximately 60 Hz, or greater. The current in the coils should be great enough to create a magnetic field in the tissue being treated which is sufficient to induce an electric field at 60 Hz which is greater than about 10 microvolts/meter. At frequencies above 60 Hz, the magnetic field may remain the same as that calculated above for the 60 Hz condition. At frequencies below 60 Hz, the magnetic field should increase inversely with the decrease in frequency. Thus, for example, at 20 Hz the magnetic field should be 3 times that needed at 60 Hz.

Figure 3:
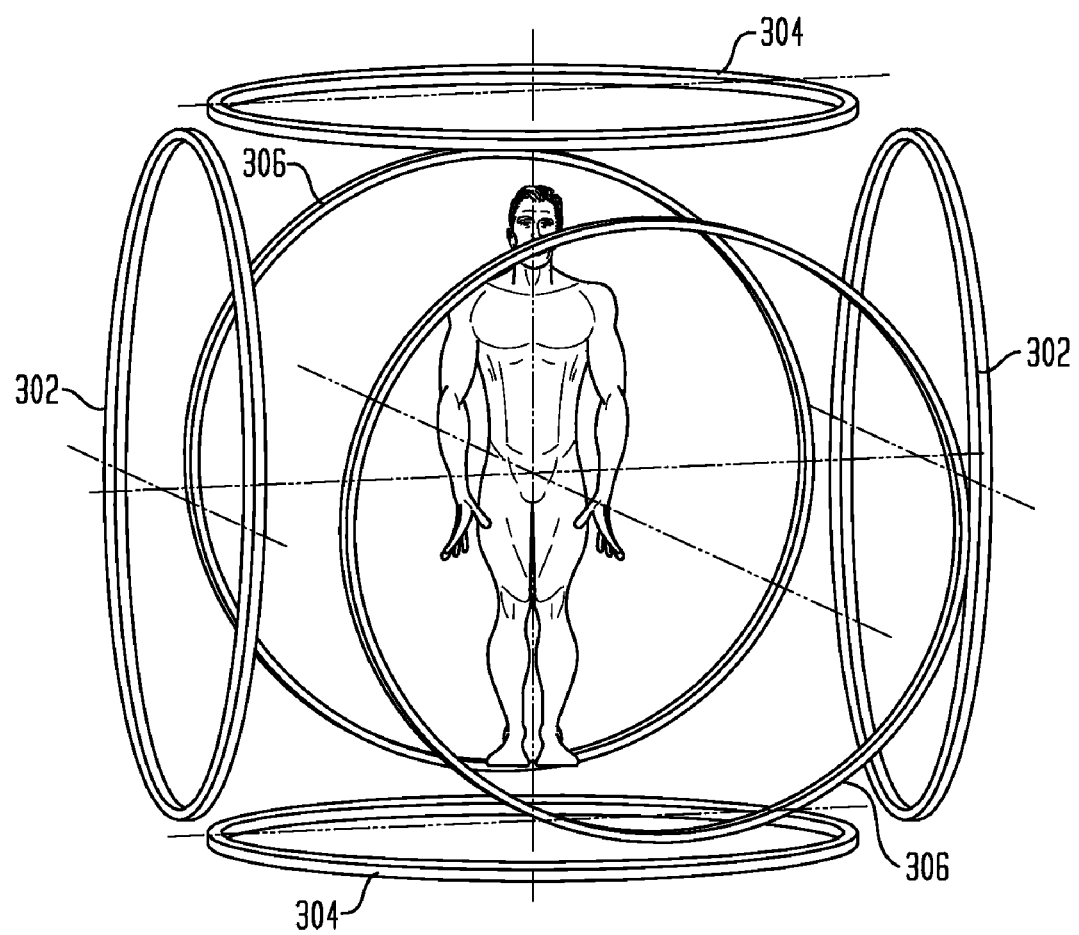
FIG. 3 is a schematic representation of a coil arrangement in accordance with an embodiment of the present invention using 3 pairs of coils.

For use in the present invention, any suitable magnetic field generating coils may be used, including, Helmholtz coils, etc. FIGS. 1, 2 and 3 show schematic representations of coil arrangements, and should not be construed to limit the application of the present invention to such arrangements. Coils of the present invention may be of various shapes and arrangements now known or later developed.

The present invention may be used in various treatment protocols including single treatments or multiple treatments on one day, in one week, or over several weeks or months, depending on the particular application. A single treatment may be provided for a period of seconds, minutes or hours depending on the particular application.

The present invention improves the effectiveness of magnetic field therapy when treating various organs in the body for conditions ranging from cancer to heart attacks. In addition, when time varying magnetic fields are used as a prophylactic to protect against adverse stresses, the present invention makes the process more effective. Thus, the present invention may be used in combination with known or later developed methods, such as those described in U.S. patent application Ser. Nos. 09/737,546 and 10/426,720, which relate the use of EMFs and temporal constancy requirements to the ability to focus the biological effect of an EMF, the entire contents and disclosures of which are hereby incorporated by reference.

The following data show the impact of the present invention. Studies were conducted to investigate the ability of induced electric fields in a rat heart to protect against a simulated heart attack. In this study, magnetic fields were applied in only one of 2 directions (vertical or horizontal linear, relative to the rat). As may be seen in the data presented in Table 1 below, no statistically significant reduction in necrotic heart tissue was observed. This was because large regions of the heart muscle were not being exposed to an electric field capable of inducing a biological effect (in this case, ischemic protection).

TABLE 1

Effect of EMFs on Damage after Heart Attack

| | | Damage (Infarct Size)* | |
|---|---|---|---|
| EMF Exposure Polarization | # Pairs | Control | EMF Exposure |
| Vertical Linear | 4 | 63.9 ± 3.2 | 60.8 ± 2.7 |
| Horizontal Linear | 4 | 57.3 ± 2.2 | 53.7 ± 1.9 |

*Data expressed as mean ± SEM

In further studies, however, it was discovered that by changing in time the direction of the applied magnetic field, such that more than one plane of magnetic field application was used during the exposure, a three-fold improvement in salvage of the myocardial tissue could be obtained. In this second study, rats were exposed either to a circularly polarized field (in the vertical or horizontal plane), or a field in which the direction of the applied magnetic field switched from vertical to horizontal every 30 seconds. In these experiments, a reduction of ~15% in necrotic tissue was observed compared to the reduction of ~5% in Table 1.

TABLE 2

Effect of EMFs on Damage after Heart Attack

| | | Damage (Infarct Size)* | |
|---|---|---|---|
| EMF Exposure Polarization | # Pairs | Control | EMF Exposure |
| Vertical Circular | 6 | 54.0 ± 3.6 | 46.5 ± 2.2$^\perp$ |
| Horizontal Circular | 6 | 51.4 ± 5.1 | 43.9 ± 4.6$^\perp$ |
| 30 Sec-Alternating Between Vertical Linear, and Horizontal Linear | 8 | 59.5 ± 1.3 | 52.4 ± 2.1$^\perp$ |

*Data expressed as Mean ± SEM
$^\perp$P < 0.05 vs. control by paired T-Test (very significant)

As is summarized in Tables 1 and 2 above, all of the linear, one-directional EMFs (vertical or horizontal) were only marginally effective in reducing the infarct size following simulated heart attack. This is to be expected given the non-uniform nature of the electric fields induced by these one-directional exposures. However, the other EMF exposures tested (vertical circular, horizontal circular or alternating) resulted in significant improvements in reduction of heart damage. These findings support the notion that multi-direction EMF exposures are capable of inducing more uniform electric fields, and thus, significant biological effects in the tissue.

Figure 4:
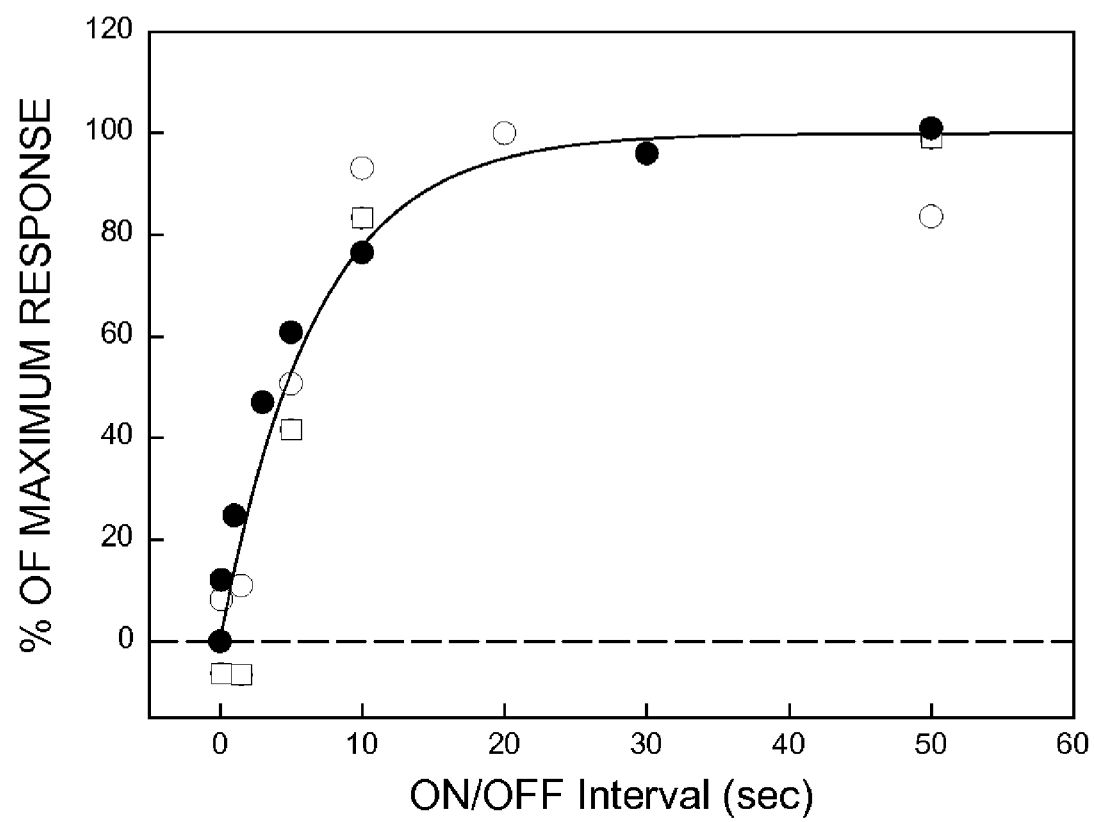
FIG. 4 is a graph of on/off intervals and percentage of maximum response for different models of EMF-induced effects, including hypoxia protection (circles) and changes in enzyme activity (squares).

According to an embodiment of the present invention, a multi-directional, magnetic field exposure approach may be coupled with specific timing protocols in order to increase its effectiveness. Specific time scales for exposure induce a more robust biological effect. It has previously been described that if a magnetic field exposure is temporally constant for some minimal period of time, for example, greater than approximately 10 seconds, a full biological effect may be achieved. FIG. 4 shows this phenomenon for a number of different models of EMF-induced effects, including hypoxia protection (circles) and changes in enzyme activity (squares). As may be seen in FIG. 4, according to an embodiment of the present invention, a minimum on/off time interval of approximately 10 seconds achieves a maximum induced biological effect. Thus, in an embodiment of the present invention, the direction of the field is not switched on time scales less than about 10 seconds. In other embodiments, however, the time scales may be more or less than 10 seconds between switching field direction.

Furthermore, whereas all uniaxial exposures create inhomogeneous induced electric fields in the tissue, most multi-axial exposures do this as well. This is because, when tissues are exposed to multi-directional fields simultaneously, the actual applied field is a sum of all the different-direction applied fields, resulting in a one-directional magnetic field exposure vector. In order to avoid this scenario, the multi-directional exposures may be applied other than simultaneously. One way to achieve this is through the use of a circularly-polarized magnetic field, whose direction continually changes (e.g., vertical or horizontal circular shown in Table 2 above). However, this method yields induced electric fields that are more difficult to quantify and is not always the most effective means of inducing electric fields in tissue, since there may still be regions with sub-threshold induced electric fields. Instead, according to an embodiment of the present invention, the use of applied magnetic fields (linear or circular), whose direction/orientation changes at certain time intervals to a second plane of exposure (as evidenced by the alternating linear data given in Table 2) is provided. If a magnetic field exposure is temporally constant for some minimal period of time (for example, greater than approximately 10 seconds), a full biological effect may be achieved.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of delivering an electric field to a body, comprising:
    delivering a first magnetic field from a first coil in a first orientation to a body and directed at a desired target within the body; and
    delivering a second magnetic field from a second coil in a second orientation directed at said desired target within the body to induce an electric field across said desired target, wherein only one magnetic field is delivered to the body at any one time.

2. The method of claim 1, wherein at least one of said first magnetic field in a first orientation and said second magnetic field in a second orientation comprises a linearly polarized magnetic field.

3. The method of claim 1, wherein at least one of said first magnetic field in a first orientation and said second magnetic field in a second orientation comprises a circularly polarized magnetic field.

4. The method of claim 1, wherein at least one of said first coil and said second coil comprises a coil pair.

5. The method of claim 1, wherein said first orientation is perpendicular to said second orientation.

6. The method of claim 1, further comprising delivering a third magnetic field from a third coil in a third orientation.

7. The method of claim 6, wherein said first orientation, said second orientation and said third orientation are each perpendicular to the orientations of the other coils.

8. The method of claim 1, wherein said first magnetic field is delivered in said first orientation for at least 5 seconds before the delivery orientation is changed to said second orientation of said second magnetic field.

9. The method of claim 1, wherein said first magnetic field is delivered in said first orientation for at least 10 seconds before the delivery orientation is changed to said second orientation of said second magnetic field.

10. The method of claim 1, wherein said first magnetic field is delivered in said first orientation for at least 30 seconds before the delivery orientation is changed to said second orientation of said second magnetic field.

11. The method of claim 1, wherein said first magnetic field is delivered in said first orientation for no more than 300 seconds before the delivery orientation is changed to said second orientation of said second magnetic field.

12. The method of claim 1, wherein the magnetic fields are delivered to the body for a total of approximately 30 minutes to approximately 60 minutes.

13. The method of claim 1, wherein the target comprises cancer cells.

14. The method of claim 1, wherein the target comprises heart tissue.

15. The method of claim 1, wherein an AC current flows alternately through said first coil and said second coil.

16. The method of claim 15, wherein the AC current flowing through said first coil is approximately 90 degrees out of phase with the AC current flowing through said second coil.

17. The method of claim 15, wherein the AC current flowing through said first coil is from approximately 60 degrees to approximately 120 degrees out of phase with the AC current flowing through said second coil.

* * * * *